(12) United States Patent
Räther et al.

(10) Patent No.: US 10,458,944 B2
(45) Date of Patent: Oct. 29, 2019

(54) TRAPPED ION MOBILITY SPECTROMETER WITH HIGH ION STORAGE CAPACITY

(71) Applicant: Bruker Daltonik GmbH, Bremen (DE)

(72) Inventors: Oliver Räther, Lilienthal (DE); Thomas Betz, Hamburg (DE); Melvin Andrew Park, Billerica, MA (US)

(*) Notice: Subject to any disclaimer, the term of this patent is extended or adjusted under 35 U.S.C. 154(b) by 0 days.

(21) Appl. No.: 15/172,237

(22) Filed: Jun. 3, 2016

(65) Prior Publication Data

US 2017/0350860 A1    Dec. 7, 2017

(51) Int. Cl.
| | | |
|---|---|---|
| *G01N 27/62* | (2006.01) |
| *H01J 49/00* | (2006.01) |
| *H01J 49/42* | (2006.01) |
| *H01J 49/06* | (2006.01) |

(52) U.S. Cl.
CPC ........ *G01N 27/622* (2013.01); *H01J 49/0031* (2013.01); *H01J 49/06* (2013.01); *H01J 49/426* (2013.01); *H01J 49/4215* (2013.01); *H01J 49/4225* (2013.01)

(58) Field of Classification Search
CPC .. H01J 49/0031; H01J 49/4125; H01J 49/425; H01J 49/063; G01N 27/622
See application file for complete search history.

(56) References Cited

U.S. PATENT DOCUMENTS

| | | |
|---|---|---|
| 7,838,826 B1 | 11/2010 | Park |
| 8,766,176 B2 | 7/2014 | Park et al. |
| 9,304,106 B1 | 4/2016 | Park et al. |
| 2002/0121594 A1* | 9/2002 | Wang ................... H01J 49/4225 250/281 |
| 2003/0132379 A1 | 7/2003 | Li |
| 2006/0016981 A1* | 1/2006 | Park ....................... H01J 49/063 250/288 |
| 2007/0084998 A1* | 4/2007 | Franzen ................ H01J 49/004 250/287 |
| 2009/0032700 A1* | 2/2009 | Park .................... H01J 49/4295 250/282 |
| 2009/0189073 A1* | 7/2009 | Yamaguchi ........... H01J 49/009 250/288 |
| 2010/0308218 A1* | 12/2010 | Wang .................... H01J 49/063 250/292 |

(Continued)

FOREIGN PATENT DOCUMENTS

| | | |
|---|---|---|
| GB | 2470664 A | 12/2010 |
| GB | 2499587 A | 8/2013 |
| WO | 2013067366 A2 | 5/2013 |

OTHER PUBLICATIONS

Michelmann, Karsten et al., Fundamentals of Trapped Ion Mobility Spectrometry, J. Am. Soc. Mass. Spectrom., Oct. 21, 2014, pp. 14-24, vol. 26, American Society for Mass Spectrometry.

*Primary Examiner* — Nicole M Ippolito
*Assistant Examiner* — Sean M Luck
(74) *Attorney, Agent, or Firm* — Benoit & Côté Inc.

(57) ABSTRACT

The invention is related to a trapped ion mobility spectrometer (TIMS device) and proposes to use higher order (order N>2) linear multipole RF systems to accumulate and analyze ions at an electric DC field barrier, either pure higher order RF multipole systems or multipole RF systems with transitions from higher order towards lower order, e.g. from a linear octopolar RF system (N=4) to a linear quadrupole RF system (N=2) in front of the apex of the electric DC field barrier.

20 Claims, 7 Drawing Sheets

(56) References Cited

U.S. PATENT DOCUMENTS

| | | | |
|---|---|---|---|
| 2011/0084205 A1* | 4/2011 | Makarov | H01J 49/0045 250/282 |
| 2012/0273670 A1* | 11/2012 | Park | G01N 27/626 250/282 |
| 2012/0273673 A1* | 11/2012 | Park | G01N 27/624 250/283 |
| 2012/0286156 A1* | 11/2012 | Park | G01N 27/622 250/282 |
| 2013/0075602 A1* | 3/2013 | Stoermer | H01J 49/0045 250/283 |
| 2013/0264477 A1* | 10/2013 | Martin | H01J 3/22 250/307 |
| 2013/0306861 A1 | 11/2013 | Papanastasiou et al. | |

* cited by examiner

TRAPPED ION MOBILITY SPECTROMETER WITH HIGH ION STORAGE CAPACITY

BACKGROUND OF THE INVENTION

Field of the Invention

The invention relates to devices and methods for the separation of ions according to their mobility.

Description of the Related Art

U.S. Pat. No. 7,838,826 (M. A. Park, 2008) discloses a compact ion mobility analyzer/spectrometer which has become known under the acronym "TIMS" (trapped ion mobility spectrometer). The length of the ion mobility separation unit inside the TIMS device preferably amounts to about five centimeters only. In a gas-tight tube with an inner diameter of about eight millimeters, an RF ion guide (RF system) generates a radial quadrupolar RF field to hold ions near to the axis. Along the axis of the RF ion guide, an electric DC field exhibits a slowly increasing ramp of an electric DC field barrier. A moving gas drives entrained ions against the electric DC field ramp where the ions are axially trapped and separated according to their mobilities at locations on the electric DC field ramp at which the friction force of the moving gas equals the force of the electric DC field. After loading the TIMS with ions, the electric DC field barrier is steadily decreased; this scan releases the ion species in the order of their relative mobilities. Unlike many other trials to build a compact ion mobility analyzer/spectrometer, the TIMS device by M. A. Park has already achieved, with adjusted low scan speeds, ion mobility resolutions up to $R_{mob}=400$ which is extraordinarily high compared to other types of mobility analyzers/spectrometers.

FIG. 1 shows the operation of a typical TIMS device. Entrained by a gas (7), ions from an electrospray ion source (not shown) are introduced via capillary (8) into the first chamber of a vacuum system. A repeller plate (9) drives the ions (6) into the entrance of RF funnel (10) which transfers them towards the TIMS device. An RF ion funnel (10, 12) usually is built as a stack of apertured diaphragms (apertured electrodes) the openings of which taper to smaller diameters thus forming an inner volume in the shape of a funnel. The two phases of an RF voltage are applied alternately to the aperture electrodes to build up a pseudopotential which keeps the ions away from the funnel walls. The ions are driven to and through the narrow end of the funnel by a moving gas, or by an additional DC potential gradient along the electrodes.

The funnel (10) guides the ions into a quadrupole RF tunnel (11) of the TIMS device. The quadrupole tunnel (11) comprises a stack of thin electrodes with central holes which form a circular gas-tight tube arranged around the axis of the TIMS device. The thin electrodes are separated by insulating material closing the gaps between the electrodes around the tube. Each electrode of the quadrupole tunnel (11) is preferably manufactured as printed circuit board (PCB) and is segmented into quadrants (1, 2, 3, 4), for generating a radial quadrupolar electric RF field inside the quadrupole tunnel (11). The quadrants (1, 2, 3, 4) of the tunnel electrodes are shown at the top of FIG. 1 together with equipotential lines of the quadrupolar RF field at a given time.

Inside the quadrupole tunnel (11), the ions are blown by the gas flow (14) against the ramp of an axial electric DC field barrier. In the bottom part of FIG. 1, two phases of the profile of the axial electric DC field barrier are shown (A and B). Between z-positions (20) and (23), the electric DC field increases linearly, generated by a quadratically increasing electric potential. Between z-positions (23) and (24), the field remains constant, forming a plateau of the electric DC field barrier, generated by a linear increase of the electrical potential. In a simple device, for instance, the complete field profile can be generated by a single voltage, applied to the diaphragm electrode at location (24), and divided by precision resistors along the diaphragm electrodes of the spectrometer tube. The resistors between location (20) and (23) increase linearly, while the resistors between (23) and (24) have equal resistance. In more complex devices, non-linear field profiles may be generated, even adjustable electric DC field profiles, e.g. by digital-to-analog converters (DAC).

The operation typically starts with an "ion accumulation phase" (A). A voltage difference on the order of 300 volts produces the electric DC field barrier. The ions are blown by the gas flow, symbolically indicated by the arrows (16), against the field barrier and are stopped there because they cannot surmount the electric DC field barrier. It should be noted that the arrows (16) represent the maximum gas velocity of a parabolic gas velocity distribution (14). The ions are accumulated on the rising edge (ramp) of the electric DC field barrier between locations (20) and (23), where ions of low mobility (mainly heavy ions of large collision cross section) collect in the high field near the upper end of the ramp, whereas ions of high mobility gather in the low field near the foot of the ramp, as indicated by the size of the dots symbolizing the size of the ions. In a second phase (B), the "scan phase", the supply voltage for the electric DC field barrier is steadily decreased, and ions of increasing mobility are released towards an ion detector, particularly to a mass spectrometer operating as ion detector.

A measured total ion current curve of the released ion species presents directly the ion mobility spectrum from low ion mobilities to high ion mobilities. The device is denominated "TIMS" (trapped ion mobility spectrometer). Regarding the theoretical basis, see the research article "Fundamentals of Trapped Ion Mobility Spectrometry" by K. Michelmann, J. A. Silveira, M. E. Ridgeway and M. A. Park published in the Journal of American Society of Mass Spectrometry (2015, Volume 26(1), pages 14-24).

Improvements of the scan modes for a TIMS device have been made to achieve a linear mobility scale, a constant resolution along the mobility scale, or a temporal zoom (M. A. Park et al., U.S. Pat. No. 8,766,176). U.S. patent application Ser. No. 14/931,125 (M. A. Park and O. Räther) describes a spatial zoom.

The ion mobility resolution $R_{mob}$ of a TIMS device was found to depend on the scan speed and gas velocity. The lower the scan speed, the higher the resolution. As already mentioned, ion mobilities of $R_{mob}=400$ have been achieved with the compact apparatus using slow scans. Because the ions generated in the ion source are lost during the scan phases, the duty cycle (or the utilization rate of the ions) depends on the ratio of the accumulation time $t_a$ to the scan time $t_s$.

A trapped ion mobility spectrometer with parallel ion accumulation is described in U.S. patent application Ser. No. 14/614,456 ("Trapping Ion Mobility Spectrometer with Parallel Accumulation", M. A. Park and M. Schubert); it improves the utilization of the ions transferred from the ion source to nearly 100%. TIMS with parallel accumulation (in the following abbreviated "PATIMS") collects the transferred ions and sequentially separates them according to their mobility, as long as space charge effects do not impair further collection of ions. PATIMS provides the unique possibility to prolong the ion accumulation duration and thus to find more detectable ion species, whereby the ion mobility resolution can even be increased by an identical prolongation of the scan time. The ions are preferably collected in an accumulation unit which is almost identical to the scanning unit, i.e. the ions are collected at a ramp of a first electric DC field barrier and are spatially separated along the ramp according to their ion mobility. Therefore, the accumulated ions are less influenced by space charge than other types of accumulators (ion traps). Of greatest importance, however, is the unique feature of a TIMS device that an increased accumulation period allows the mobility resolution to be increased by choosing correspondingly longer scan durations, e.g. 100 milliseconds scan duration with an ion mobility resolution of $R_{mob}=90$ instead of 20 milliseconds scan duration with $R_{mob}=60$. As a consequence of the increased number of collected ions and the improved mobility resolution, more ion species can be detected and analyzed. Once an ion mobility scan is completed (optionally after twenty to one hundred milliseconds or even more), accumulated ions are transferred (in about a millisecond) from the accumulation unit to the scanning unit, and the next mobility scan is started. In total, a skilled practitioner will appreciate that it will be possible to achieve a measurement rate of 300 to 450 different ion species per second. If PATIMS is installed in a tandem mass spectrometer for acquiring fragment mass spectra, 300 to 450 characteristic fragment mass spectra per second can be measured quantitatively.

FIG. 2 schematically shows a preferred PATIMS device and its principle of operation. The RF quadrupole tunnel (11) is prolonged compared to the TIMS device shown in FIG. 1 and divided into an accumulation unit (11a) and scanning unit (11b). The gas flow (14) drives the ions through the elongated RF quadrupole tunnel (11). The PATIMS device comprises two DC voltage supply units (not shown) for generating the two electric DC field barriers within the two tunnel units (11a, 11b). The two DC voltages are applied to the electrodes at locations (33) and (37). The quadrupolar RF field inside the RF quadrupole ion tunnel (11) holds the ions on or near to the axis of the device. Chains of resistors between the apertured diaphragms in both tunnel units (11a,11b) generate the two electric DC field barriers for the ion accumulation unit (11a) and for scanning unit (11b), shown in diagram (C) below. The gas flow (16) drives the ions against the electric DC field barriers, separating the ions in space according to their ion mobility. During the ion mobility scan, the voltage applied to electrode (37) of the scan unit (11b) is steadily decreased, thereby releasing ion species with increasing mobility, which are directly measured in an ion detector resulting in an ion mobility spectrum or further analyzed in a downstream mass analyzer, respectively.

In spite of the fact that ions are accumulated at spatially separated positions according to their mobility, there is still a need for a further increased storage capacity without considerable losses of ions by space charge effects. Some improvements for higher amounts of stored ions in selected regions of ion mobility, particularly for ions of low ion mobility, are given in U.S. patent application Ser. No. 14/614,463 (M. A. Park and O. Räther, "High Duty Cycle Trapping Ion Mobility Spectrometer"). The higher loading capacity is based on non-linear electric DC field ramps, with flatter field ramps for ion species of interest, in order to diminish the effect of space charge for these ion species. For high identification rates in proteomics of complex mixtures the storage capacity needs to be further improved. It has been shown that a factor of two in the ion capacity already would greatly help, but in practice there is a need for improved methods and devices to increase the number of stored ions by at least a factor of three to five.

SUMMARY OF THE INVENTION

The invention provides a trapped ion mobility analyzer (also termed TIMS device here) with an RF ion guide that generates an RF multipole field with an order higher than an RF quadrupolar field (N=2). The trapped ion mobility analyzer preferably comprises an electric DC field gradient (ramp) and a counteracting gas flow that drives ions against the electric DC field gradient such that ions are axially trapped in the RF ion guide. The direction of the gas flow can be directed upstream towards an ion source or downstream away from the ion source. Most preferably, the electric DC field gradient is the rising edge of an electric DC field barrier having an apex or a plateau whereas the counteracting gas flow drives the ions away from the ion source against the barrier. The trapped ion mobility analyzer can also comprise a gas flow with a velocity gradient and a counteraction (constant) electric DC field. The trapped ions are released from the ion guide according to their mobility by adjusting the electric DC field and/or the gas flow.

In one embodiment, the trapped ion mobility analyzer preferably comprises an electric DC field barrier and a counteracting gas flow that drives ions against the electric DC field barrier wherein the RF multipole field with order N>2 extends along the electric DC field barrier. The RF ion guide can additionally generate an RF quadrupolar field (N=2) which is substantially weaker than the RF multipole field with order N>2.

In another embodiment, the RF ion guide can additionally generate an RF quadrupolar field (N=2) which is substantially weaker than the RF multipole field with order N>2 along a first portion of the ion guide and which is substantially stronger than the RF multipole field with order N>2 along a second portion of the ion guide. The trapped ion mobility analyzer preferably comprises an electric DC field barrier and a counteracting gas flow that drives ions the against electric DC field barrier wherein the RF quadrupolar field is stronger than the RF multipole field with order N>2 adjacent to the apex and/or on the apex of the electric DC field barrier. Most preferably, the electric DC field barrier comprises a plateau and the RF quadrupolar field is stronger than the RF multipole field with order N>2 adjacent to the beginning and along at least a part of the plateau.

In another embodiment, the RF multipole field with order N>2 can transition into an RF multipole field of lower order along the RF ion guide. The RF ion guide can for example comprise a system of 16 rows of inner electrodes which are supplied with electric RF potentials and generate a transition from an octopolar RF multipole field into a quadrupolar RF field. The ion guide can also comprise a system of 24 rows of inner electrodes which are supplied with electric RF potentials and generate a transition from a dodecapolar RF field, optionally via a hexapolar RF field, into a quadrupolar RF field.

In another embodiment, the trapped ion mobility analyzer preferably comprises an electric DC field barrier and a counteracting gas flow wherein the laminar gas flow is formed by a gas-tight tube which has a greater inner diameter at the entrance and a smaller inner diameter at the exit. Preferably, an RF multipole field of at least third order is generated in a segment of the tube with greater diameter, whereas a quadrupolar RF field is prevailing in a segment with smaller diameter at the exit. The tube can comprise cylindrical segments of different inner diameter with smooth transitions in between to keep the gas flow laminar. It can also comprise conical and cylindrical segments.

The RF multipole field with order N>2 can be one of a hexapolar (N=3), octopolar (N=4) and dodecapolar (N=6) RF field or an RF field of an ion guide with stacked apertured electrodes. The RF multipole field with order N>2 can even be superposition of different higher orders with N>2.

The RF ion guide of the TIMS device can be built by rolling or folding printed circuit boards (PCB's). The PCB can either be a flexible foil, e.g. a polyimide foil (KAPTON®), which can be rolled or folded for example to a tube with circular inner cross section, or a at least on partially flexible PCB which can be folded to a tube of polygonal inner cross section. All flexible or foldable PCBs preferably carry electrodes required to generate the radial electric RF field and the axial electric DC field on one side (inside of the RF ion guide), and all the electronic components needed for supplying and distributing RF and DC voltages on the other side (outside of the RF ion guide). Since the surfaces between the printed electrodes of a PCB's are endangered to be charged up by ions, the surface are preferably covered with a high-resistance coating. A variety of different procedures can be used for achieve the coating with high-resistivity material. The coating can for example be achieved by spraying a suitable two-component mixture (e.g. epoxy raisins) containing solvents with organic salts with subsequent hardening of the mixture or by evaporation of a suitable material, e.g. a semiconducting material. Specific surface resistances should amount to $10^9$ to $10^{12}$ Ohms between inner electrodes. It should further be mentioned that a polyimide foil may not sufficiently shield the voltages applied to the outside components from penetrating into the RF ion guide resulting in a disturbance of the electric RF and DC fields inside the RF ion guide. Therefore, care has to be taken to arrange the electric components in such a way that these disturbances are minimized, e.g. by a localization of the electric components in such a way that their voltages correspond to the voltages of the inner electrodes located below them.

The inner diameter of the RF ion guide is preferably between 5 and 15 millimeters, preferentially between 8 and 10 millimeters. The length of a TIMS scanning unit is preferably between 40 and 150 millimeters.

The invention further provides a mass spectrometric system comprising a trapped ion mobility analyzer with an RF ion guide, that generates an RF multipole field with an order higher than a quadrupolar RF field (N=2), and a downstream mass analyzer. The mass analyzer can be one of a time-of-flight mass analyzer with orthogonal ion injection, an electrostatic ion trap, an RF ion trap, a quadrupole mass filter, and an ion cyclotron frequency mass analyzer. The mass spectrometric system can further comprise a quadrupole mass filter and a downstream fragmentation cell which are positioned between the ion mobility analyzer and the mass analyzer.

The invention further provides a method for operating a trapped ion mobility analyzer, comprising the steps: (a) generating ions in an ion source; (b) transferring the ions into an RF ion guide; (c) radially confining the ions in the RF ion guide by an RF multipole field with an order higher than an RF quadrupolar field (N=2); (d) axially trapping the ions in the RF ion guide by an electric DC field ramp and a counteracting gas flow that drives the ions against the electric DC field ramp; and (e) releasing the trapped ions from the ion guide according to their mobility by changing the electric DC field and/or the gas flow. The amount of transferred ion species can be so high that the ion density of at least one ion species is highest at an off-axis position along a part of the RF ion guide or along the complete RF ion guide due to the space charge of the transferred ions. In one embodiment, the at least one ion species is released from the ion guide at an off-axis position. In another embodiment, the ions are radially confined by an RF multipole field with an order N>2 along an upstream part of the RF ion guide and by a quadrupolar RF field along a more downstream part of the RF ion guide wherein the ions are released from the ion guide on-axis at the more downstream part of the RF ion guide.

The invention is based on the fact that linear RF multipole ion storage cells (ion traps) with more than four poles (multipole order N>2) take up considerably more ions than a quadrupole ion storage cell (N=2), however, the ions are less concentrated in a space near the axis of the linear RF ion trap. Within octopole (N=4) and higher order multipole RF ion guides, the space near the axis is even almost empty when the number of ions approaches space charge limits. The spatial ion distribution (ion cloud) of a single ion species takes the form of lengthy cylinder, which is also spread in an axial direction by the space charge effect. TIMS, however, was hitherto thought to require the ions to be accumulated on the axis of the RF ion guide because they have to be driven over the electric DC field barrier by the central part of the gas flow at the apex of its parabolic velocity distribution. For non-central ion distributions, the ion mobility resolution was assumed to decrease considerably. In contrast, however, experiments and simulation have revealed that releasing ions from higher order RF ion guides (RF multipole systems) shows surprisingly good mobility resolution.

The invention proposes to use higher order (N>2) multipole RF systems to accumulate high numbers of ions on the ramp of an electric DC field barrier, either pure higher order RF multipole systems, or multipole RF systems with a transition from higher order towards a lower order; e.g. from an octopolar RF system (N=4) optionally via a hexapolar RF system (N=3) to a quadrupolar RF system (N=2) near the end of the TIMS device, preferably in front of apex of the electric DC field barrier.

The ion capacity can be further increased by a TIMS tube which is wider at the entrance and narrower towards the exit, whereby a higher gas velocity near the exit is even advantageous for the ion mobility separation.

Electronic components (55), particularly capacitors and resistors, are positioned at the outside of the flexible PCB foil and used to supply RF and correctly divided DC voltages to the rows of inner electrodes (51-54). The position of the electric components of each voltage divider at the outside of the flexible PCB foil is preferably selected to correspond with the DC voltages at the inner electrodes to minimize the disturbances of the fields inside the quadrupole tunnel (50) by the voltages at the outside electric components. Four contacts (+RF, −RF, +/−DC, and DC ground) serve to connect with the corresponding voltage generators. The +/−DC contact corresponds to location (24) in FIG. 1. A positive +/−DC is used for positive ions, a negative voltage for negative ions. During the ion mobility scan, +/−DC is steadily approaching ground, as shown in Diagram B of FIG. 1. If the shape of the electric field profile is fixed, the TIMS device needs only a two-phase RF voltage and a single DC voltage delivered from suitable generators.

Figure 3:
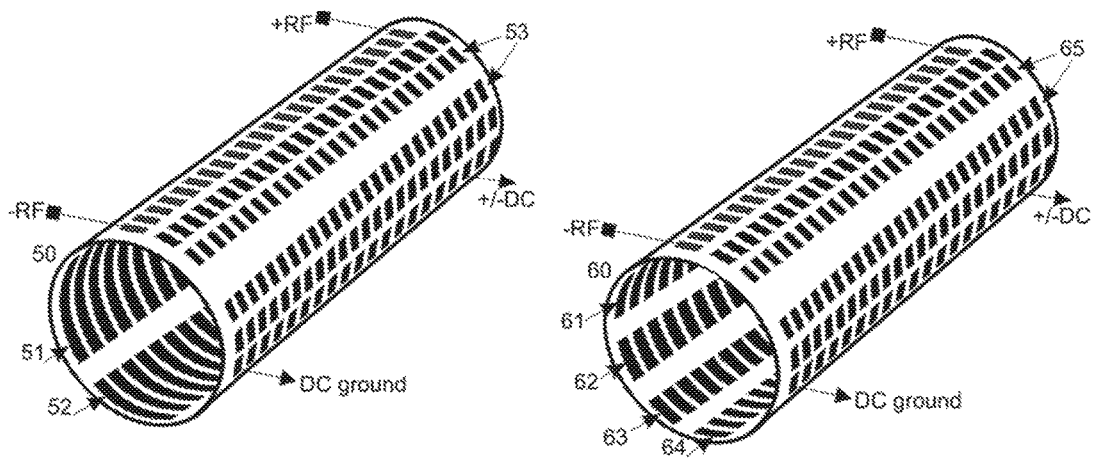
FIG. 3 shows, at the left-hand side, a system of electrodes utilized in a TIMS device. Instead of using a stack of apertured electrodes manufactured as rigid PCBs (printed circuit boards), a flexible PCB foil, e.g. a polyimide foil (KAPTON®), carrying four rows (51-54) of inner electrodes is rolled to form a quadrupole tunnel (50) of the TIMS device to generate the radial RF and axial DC fields. The electrode rows (53) and (54) are not visible in FIG. 3. The inner electrodes along the rows preferably have periods of one to two millimeters, resulting in at least 20, and up to 150 electrodes per row. A preferred number is around 50 inner electrodes per row.

A rolled RF ion guide can be easily built also with a radial RF octopole field (N=4) inside. At the right-hand side, FIG. 3 shows a rolled RF ion guide (60) utilized in a TIMS device with an octopolar RF field, comprising eight rows (61-64) of inner electrodes. In an analog manner, RF ion guides with hexapolar (N=3) or even dodecapolar (N=6) RF fields may be fabricated.

Figure 4:
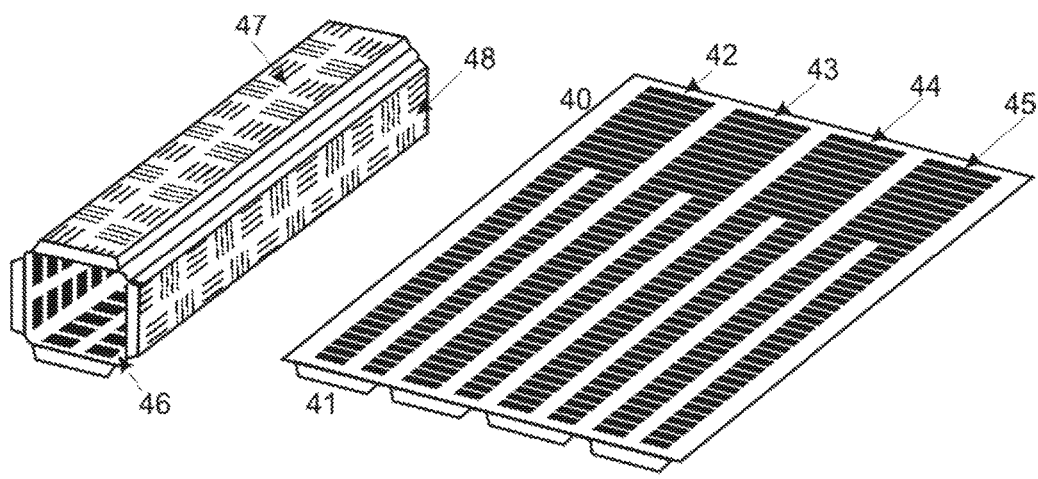

FIG. 4 shows a system of electrodes used for a TIMS device. A flexible PCB foil (40) is folded to form a rectangular RF ion guide comprising inner electrodes for generating an octopolar RF field at the entrance, and for generating an RF quadrupole field at the exit. At the right-hand side, the flexible PCB foil (40) is unfolded, showing eight rows of inner electrodes at the entrance and four rows at the exit. Every other row is connected to the same phase of the RF voltage; neighboring rows are connected to different phases. The different electrodes of the rows are supplied with different DC voltages to generate the axial electric DC field profile in the RF ion guide. At the left-hand side, the flexible PCB foil (40) is folded to a tube with rectangular inner cross section. The outside surfaces (47) and (48) of the flexible PCB foil (40) carry the capacitors and resistors needed to supply the RF and to divide the DC voltages for the inner electrodes (46), shown in a schematic way only.

Figure 5:
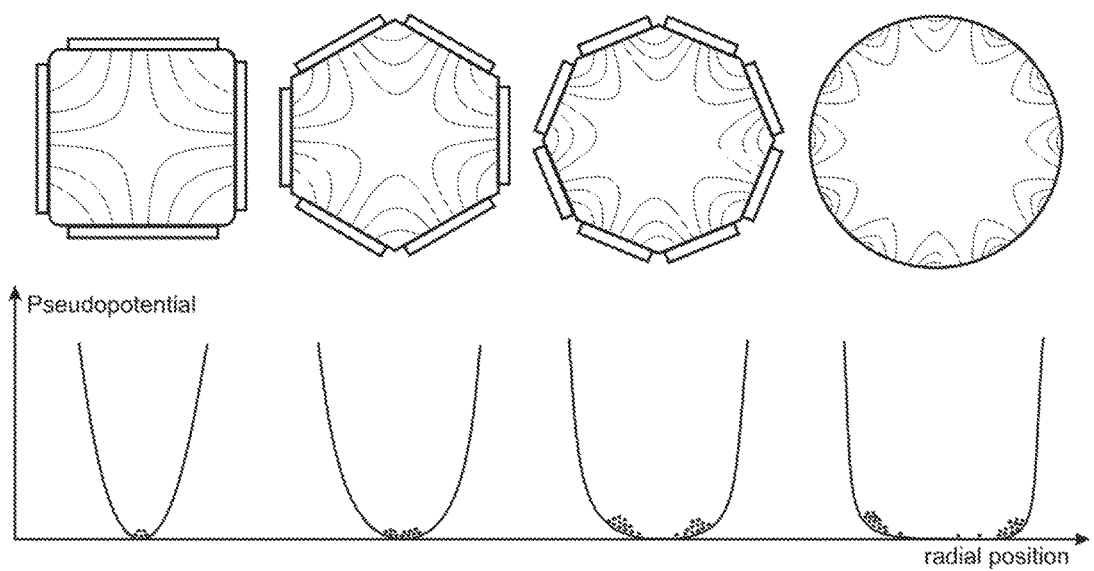

FIG. 5 shows cross sections of RF ion guides formed from folded PCB for generating a quadrupolar, hexapolar, octopolar, and dodecapolar RF field. Pseudopotential distributions generated by the RF fields in a radial direction are shown in the bottom of FIG. 5. The quadrupolar field has a strongly parabolic pseudopotential distribution, keeping the ions on the axis. The pseudopotential distributions of the hexapolar, octopolar, and dodecapolar RF field are wider at their bottom, taking up more ions before the ions get lost by space charge effects. The collection of dots illustrates schematically the number and distribution of ions near the space charge limit. Within the octopolar and dodecapolar RF field, the ions are forced by their space charge to the outside of the tube, keeping the center part empty.

Figure 1:
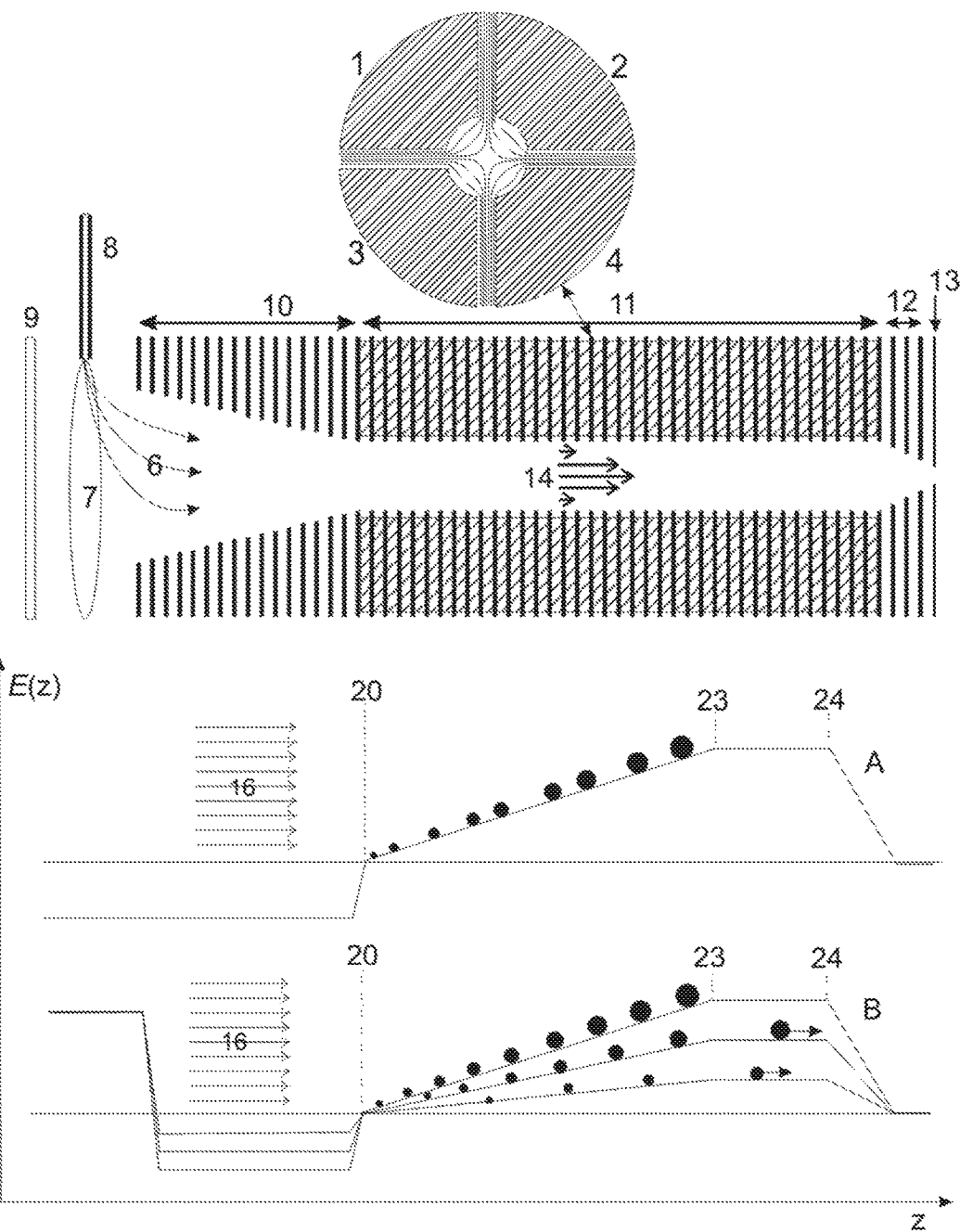
FIG. 1 shows the operation of a typical trapped ion mobility analyzer/spectrometer (TIMS device). Entrained by a gas (7), ions from an electrospray ion source (not shown) are introduced via capillary (8) into the first chamber of a vacuum system. A repeller plate (9) drives the ions (6) into an entrance RF funnel (10) of the TIMS device. The RF funnel (10) guides the ions into a quadrupole tunnel (11) (RF ion guide) of the TIMS device. The quadrupole tunnel (11) comprises a stack of electrodes with central holes which form a circular gas tide tube arranged around the z-axis of the device. The electrodes are separated by insulating material closing the gaps between the electrodes around the tube. Each electrode of the quadrupole tube (11) is preferably manufactured as printed circuit board (PCB) and is segmented into quadrants (1, 2, 3, 4) for generating a radial quadrupolar electric RF field inside which keeps the ions near to the axis. Inside the quadrupole tunnel (11), the ions are blown by the gas flow (14) against the ramp of an axial electric DC field barrier. In the bottom part of FIG. 1, two phases of the profile of the axial electric DC field barrier are shown (A and B). The operation starts with an "ion accumulation phase" (A). The ions are blown by the gas flow, symbolically indicated by the arrows (16), against the ramp of the field barrier and are stopped there because they cannot surmount the electric DC field barrier. The ions are accumulated on the rising edge (ramp) of the electric DC field barrier between locations (20) and (23), where ions of low mobility (mainly heavy ions of large collision cross section) are trapped in the high field near the upper end of the ramp, whereas ions of high mobility are trapped in the low field near the foot of the ramp, as indicated by the size of the dots symbolizing the ions. In a second phase (B), the "scan phase", the supply voltage for the electric DC field barrier is steadily decreased, and ions of increasing mobility are released towards an ion detector, particularly to a mass spectrometer operating as ion detector.
Figure 6:
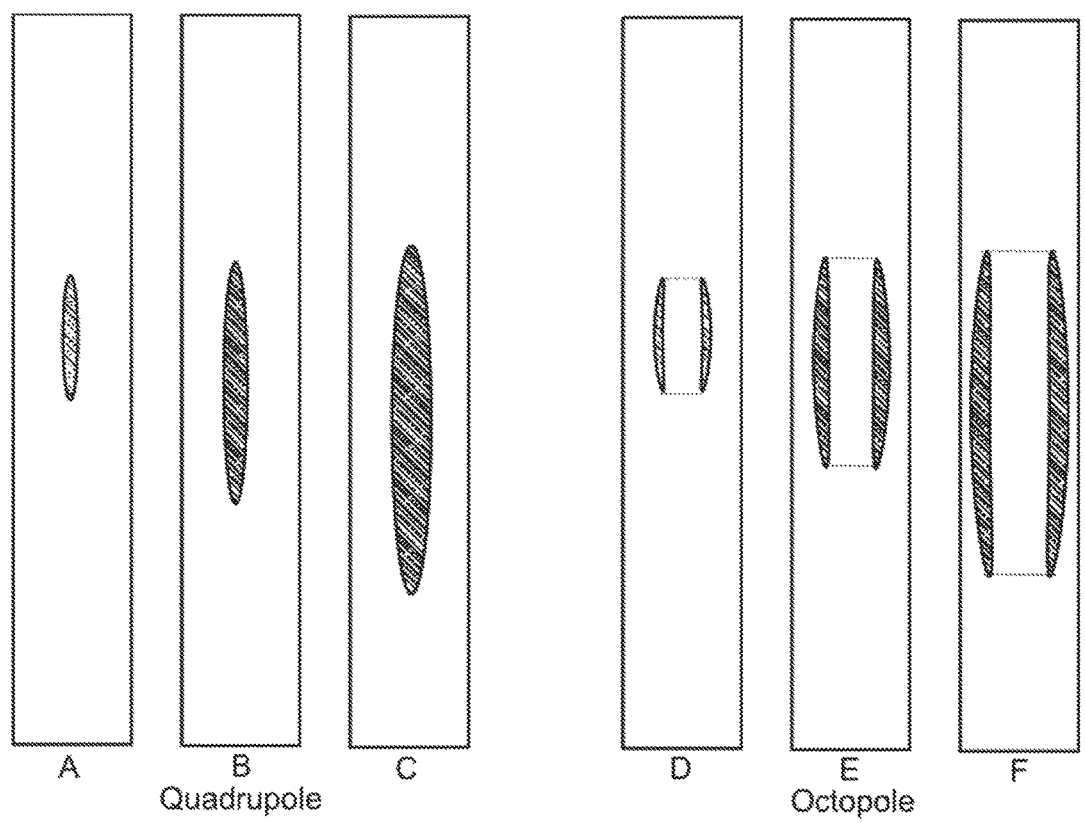

FIG. 6 shows cross sections of the RF ion guide of two TIMS devices. At the left-hand side (A, B, C), a TIMS device with a quadrupolar RF field is shown which is filled with a single ion species with different amounts of ions (A lowest amount, C highest amount). Whereas the dots in FIG. 1, representing the size of ions of different ion species, are somewhat misleading in suggesting that the ions of an ion species are spatially distributed in the RF ion guide and form ion clouds, the spatial distribution of an ion species has been found in simulations to be drawn out by space charge effects to a long spindle, rather than to a compact spherical cloud, because of asymmetric confinement forces in the radial and axial directions. At the right-hand side (D, E, F), a TIMS device with an octopolar RF field is shown which is again filled with a single ion species with different amounts of ions (D lowest amount, F highest amount). In the RF octopole field, the ion cloud of the single ion species has the shape of a cylindrical tube, i.e. that the ion density is highest at an off-axis position. In the center part of the RF ion guide, the ions are pressed to the outside because of a space charge. With higher amounts of ions, the "ion cylinder" moves closer to the inner surface of the RF ion guide and is spread in an axial direction. If more different ion species are present, the situation becomes somewhat chaotic, because the clouds are influencing each other, but during the scan of the TIMS device, the ion species leave the device one after another.

Figure 7:
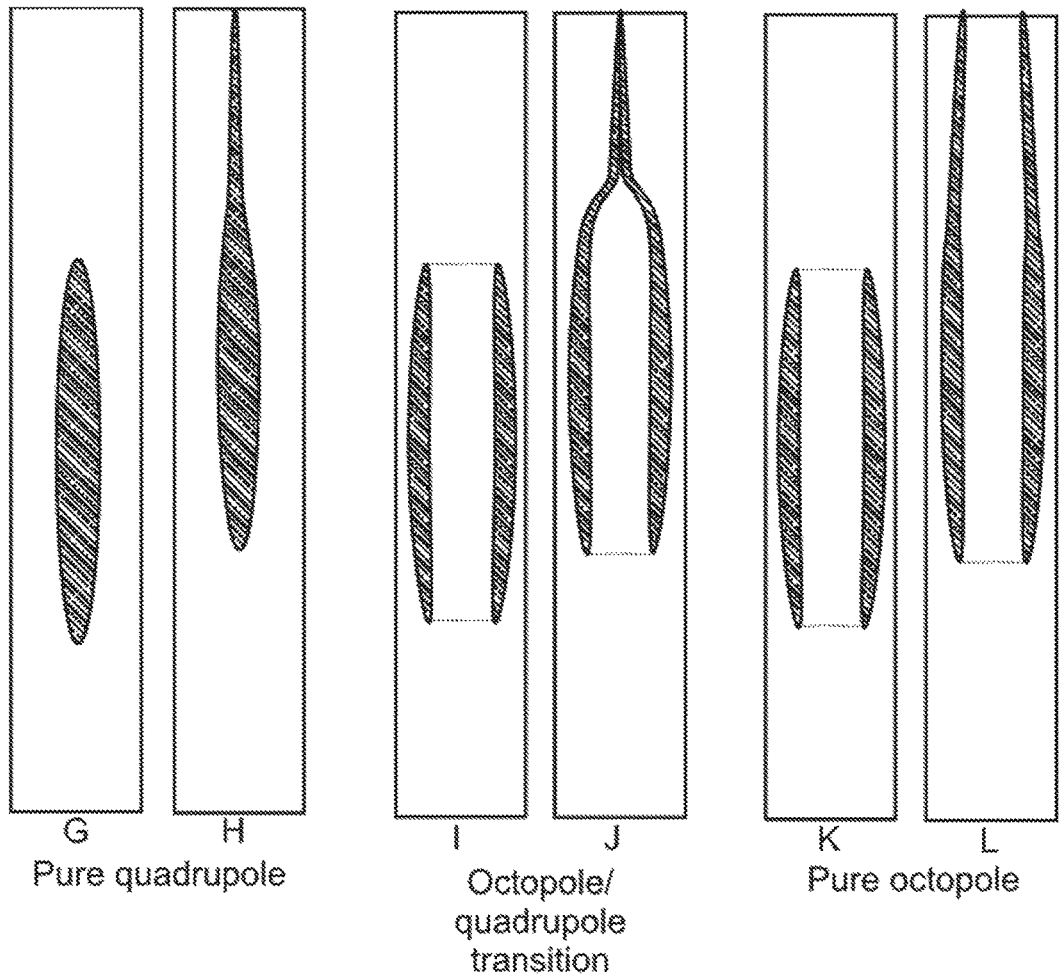

FIG. 7 shows the spatial ion distribution of a single ion species at a high ion load in three different TIMS devices during accumulation (G, I, K) and scanning (H, J, L). At the left-hand side (G, H), a TIMS device with a pure quadrupolar RF field is shown. In the center (I, J), an octopolar RF field merges into a quadrupolar RF field. In the pure octopolar RF field (right-hand side, K, L), the cylindrical ion cloud leaves without being concentrated on the axis of the RF ion guide.

Figure 8:
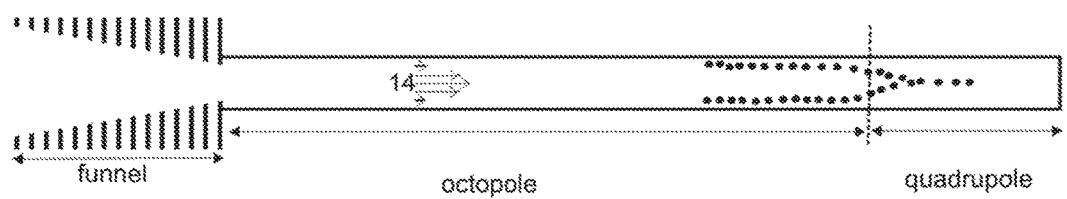

FIG. 8 shows ion trajectories in an RF ion guide of a preferred TIMS device during accumulation and scanning. The preferred TIMS device comprises an RF ion guide with a transition from an octopolar RF field to a quadrupolar RF field. The dots schematically represent the positions of ions that are first trapped and accumulated outside the axis in the octopole region and then concentrated on or near the axis downstream in the quadrupole region of the RF ion guide when they are released from the RF ion guide.

Figure 2:
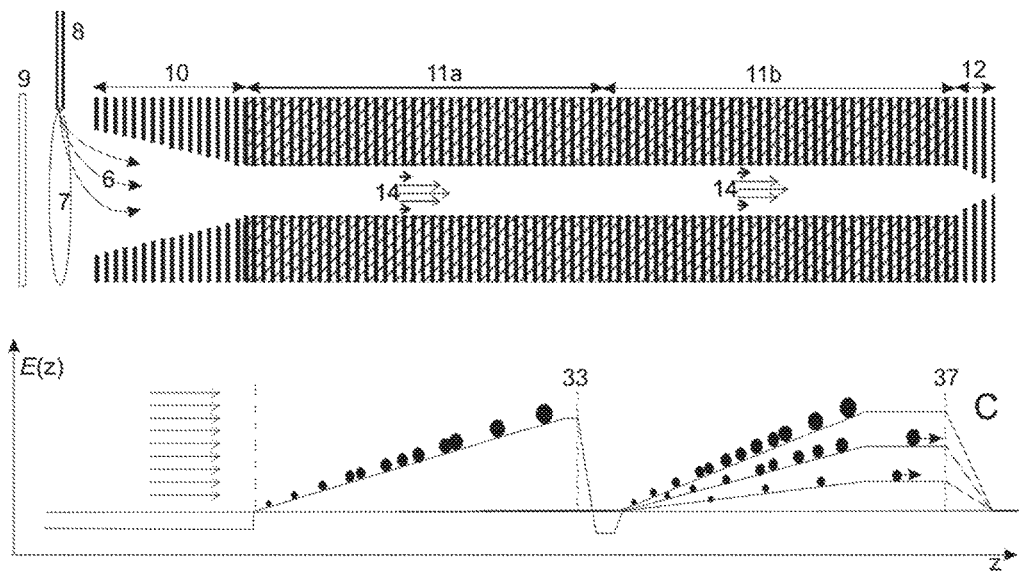
FIG. 2 shows a preferred PATTIMS device and its principle of operation. The RF quadrupole tunnel (11) is prolonged compared the TIMS device shown in FIG. 1 and is divided into an accumulation unit (11a) and a scanning unit (11b). The gas flow (14) drives the ions through the quadrupole tunnel (11). The spectrometer comprises two DC voltage supply units (not shown) for generating two electric field barriers in an axial direction within the two tunnel units (11a, 11b). The DC voltages are applied to the electrodes at locations (33) and (37). The quadrupolar RF field inside the quadrupole tunnel (11) holds the ions on the axis of the device. Chains of resistors between the apertured diaphragms in both tunnel units (11a, 11b) produce the two electric DC field barriers, one for the accumulation unit (11a) and one for the scanning unit (11b) (shown in C). The gas flow (16) drives the ions against the electric DC field barriers which are separated in space according to their ion mobility. During the mobility scan, the voltage applied to electrode (37) of the scanning unit (11b) is steadily decreased, thereby releasing ion species with increasing mobility, which are directly measured in an ion detector resulting in an ion mobility spectrum or further analyzed in a downstream mass analyzer, respectively.
Figure 9:
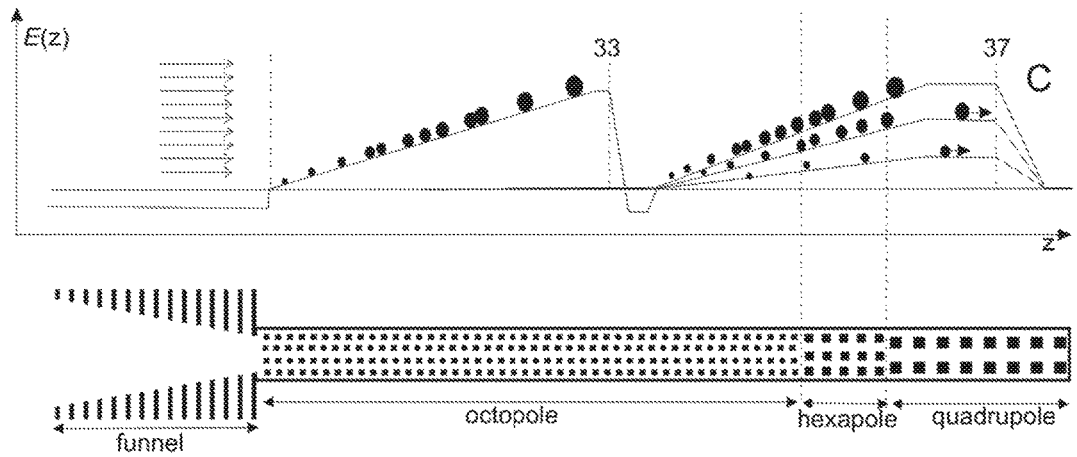

FIG. 9 shows a preferred PATIMS device according to the present invention. The electric DC profile shown in the upper part of the figure is equal to that of FIG. 2. The RF ion guide of the TIMS device generates an octopolar RF field (order N=4) at the entrance of the PATIMS device. The octopolar RF field transitions to a hexapolar RF field (N=3) in the scan unit and further to a quadrupolar RF field (N=2) at the plateau of the electric DC barrier of the scan unit. The RF quadrupole field (N=2) confines the ions near the axis of the RF ion guide adjacent to and at the apex of the electric DC field barrier.

Figure 10:
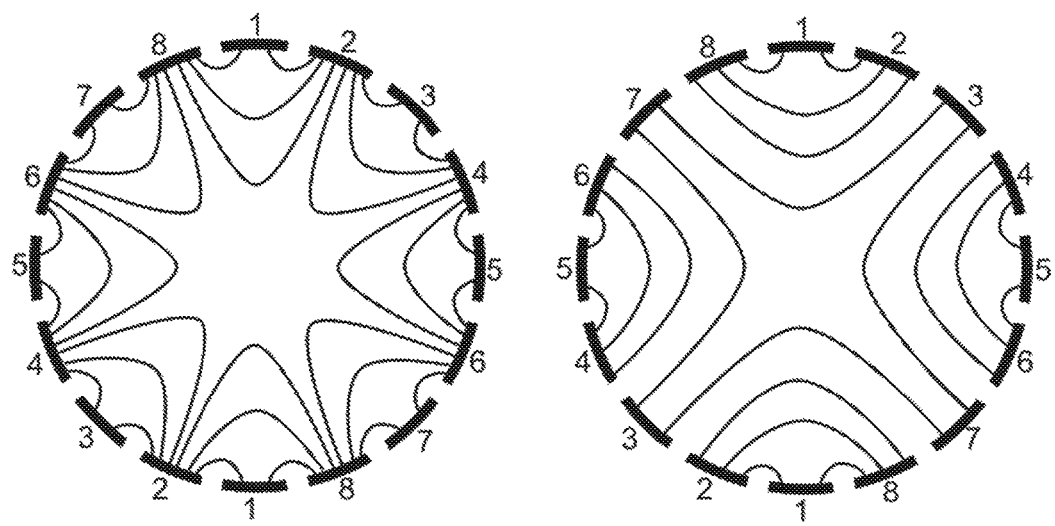

FIG. 10 shows how a smooth transition from an octopolar RF field to a quadrupolar RF field can be generated, using an electrode system with 16 rows of inner electrodes. At the left-hand side, an octopolar RF field is generated by eight electrode rows (2, 4, 6, 8), whereby the rows (2) and (6) are supplied with a first phase of an RF voltage, and the rows (4) and (8) with a second phase of the RF voltage. The residual electrode rows (1, 3, 5, 7) are kept at ground potential. At the right-hand side, a quadrupolar RF field is generated by applying a first phase of an RF voltage to electrodes (2, 3, 4) and a second phase to electrodes (6, 7, 8). Electrodes (1) and (5) are kept at ground potential. A smooth transition from the octopolar RF field can be achieved by first feeding electrodes (3) and (7) with the quadrupolar RF voltage, generating a superposition of the octopolar RF field with a quadrupolar RF field, and then removing the octopolar RF voltages at electrodes (2, 4, 6, 8) and supplying the quadrupolar RF voltage to electrode groups (2, 3, 4) and (6, 7, 8).

Figure 11:
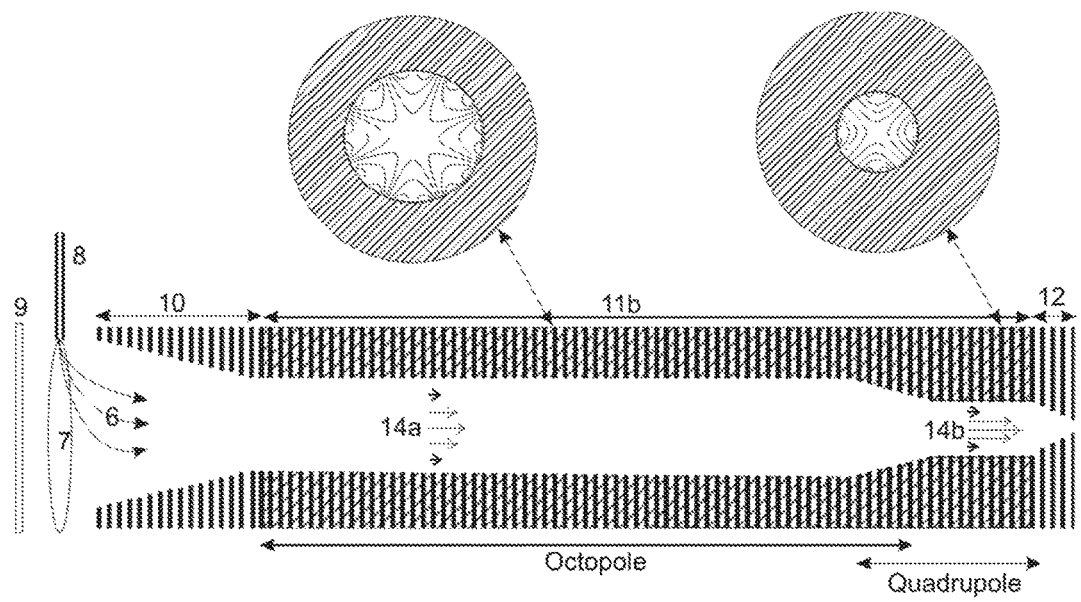

FIG. 11 shows a TIMS device with an RF ion guide (11b) which starts with a wide diameter and which generates a radial RF octopole field along an upstream portion. The RF ion guide (11b) then decreases in diameter and generates a radial RF quadrupole field in a downstream portion. Octopole and quadrupole fields are generated by a stack of apertured electrodes having the electrode structure presented in FIG. 10, allowing a smooth transition with partly overlapping RF fields of different orders. In the wider upstream portion, the gas flow (14a) is considerably slower than the gas flow (14b) in the narrower downstream portion. In the top of the figure, the equipotential lines of the radial RF fields are shown.

Figure 12:
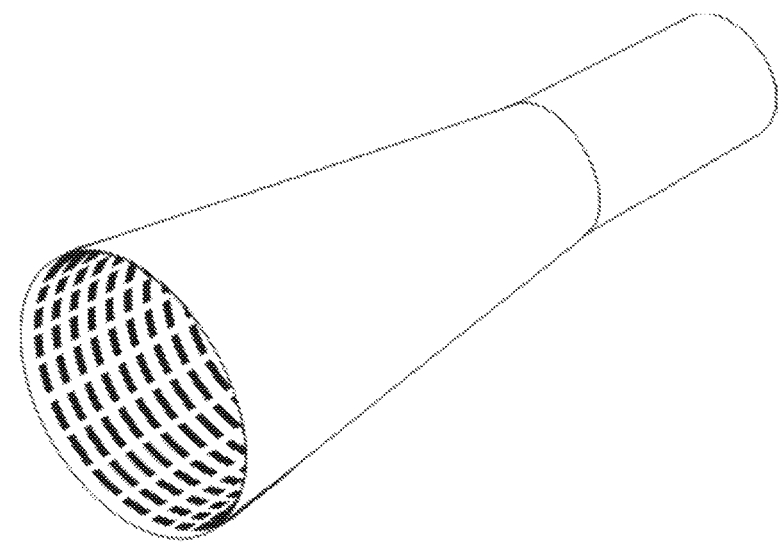

FIG. 12 shows a conical structure for a part of the TIMS device, rolled from a flexible PCB foil. The PCB foil can carry electric components for the distribution of the RF and DC voltages at the outside (not shown).

DETAILED DESCRIPTION

The invention is based on the fact that linear RF multipole ion storage cells (ion traps) with higher order multipoles (order N>2) can take up considerably more ions than a quadrupole ion storage cell (N=2), however, the ions are less or not at all concentrated in the center space near the axis of the linear RF ion trap. In addition, non-thermalized ions with some kinetic energy get more easily lost in quadrupole ion storage cells. Within octopole and higher order multipole ion guides, the space near the axis is nearly empty when the number of ions approaches space charge limits. Whereas the dots in FIG. 1, representing symbolically the size of the ions of different ion species, are somewhat misleading in suggesting that the ion clouds of these ion species are spherical, it has been found in simulations that the form of the ion clouds in quadrupolar RF fields is drawn out by space charge effects to a long spindle.

FIG. 3 shows, at the left-hand side, a system of electrodes utilized in a TIMS device. Instead of using a stack of apertured electrodes manufactured as rigid PCBs (printed circuit boards), a flexible PCB foil, e.g. a polyimide foil, carrying four rows (51-54) of inner electrodes is rolled to form an RF quadrupole tunnel (50) for generating radial RF and axial DC fields. The electrode rows (53) and (54) are not visible in FIG. 3. Electronic components (55), particularly capacitors and resistors, are positioned at the outside of the flexible PCB foil and used to supply RF and correctly divided DC voltages to the rows of inner electrodes (51-54). Four contacts (+RF, −RF, +/−DC, and DC ground) serve to connect with the corresponding voltage generators. The +/−DC contact corresponds to location (24) in FIG. 1. A positive +/−DC is used for positive ions, a negative voltage for negative ions. During the ion mobility scan, +/−DC is steadily approaching ground, as shown in Diagram B of FIG. 1. If the shape of the electric field profile is fixed, the TIMS device needs only a two-phase RF voltage and a single DC voltage delivered from suitable generators. A rolled RF ion guide can be easily built also with a radial RF octopole field (N=4) inside. At the right-hand side, FIG. 3 shows a rolled RF ion guide (60) of a TIMS device with octopolar RF field, comprising eight rows (61-64) of inner electrodes. In an analog manner, a TIMS tube with hexapolar (N=3) or even dodecapolar (N=6) RF fields may be fabricated.

FIG. 4 shows a system of electrodes used for a TIMS device. A flexible PCB foil (40) is folded to form a rectangular RF ion guide comprising inner electrodes for generating an octopolar RF field at the entrance, and for generating an RF quadrupole field at the exit. At the right-hand side, the flexible PCB foil (40) is unfolded, showing eight rows of inner electrodes at the entrance and four rows at the exit. Every other row is connected to the same phase of the RF voltage; neighboring rows are connected to different phases. The different electrodes of the rows are supplied with different DC voltages to generate the axial electric DC field profile in the RF ion guide. At the left-hand side, the flexible PCB foil (40) is folded to a tube with rectangular inner cross section. The outside surfaces (47) and (48) of the flexible PCB foil (40) carry the capacitors and resistors needed to supply the RF and to divide the DC voltages for the inner electrodes (46), shown in a schematic way only.

FIG. 5 shows cross sections of RF ion guides formed from folded PCB for generating a quadrupolar, hexapolar, octopolar, and dodecapolar RF field.

Pseudopotential distributions generated by the RF fields in radial direction are shown in the bottom of FIG. 5. The quadrupolar field has a strongly parabolic pseudopotential distribution, keeping the ions on the axis. The pseudopotential distributions of the hexapolar, octopolar, and dodecapolar RF field are wider at their bottom, taking up more ions before the ions get lost by space charge effects. The collection of dots illustrates schematically the number and distribution of ions near the space charge limit. Within the octopolar and dodecapolar RF fields, the ions are forced by their space charge to the outside of the tube, keeping the center part empty. It has been shown by simulations that an exactly circular inner cross section is not necessarily required for operating a TIMS device. Near to the axis, the gas flow has to a good approximation a parabolic velocity distribution, even in a rectilinear tube.

FIG. 6 shows cross sections of the RF ion guide of two TIMS devices. At the left-hand side (A, B, C), a TIMS device with a quadrupolar RF field is shown which is filled with a single ion species with different amounts of ions (A lowest amount, C highest amount). Whereas the dots in FIG. 1, representing the size of ions of different ion species, are somewhat misleading in suggesting that the ions of an ion species are spatially distributed in the RF ion guide and form ion clouds, the spatial distribution of an ion species has been found in simulations to be drawn out by space charge effects to a long spindle, rather than to a compact spherical cloud, because of asymmetric confinement forces in radial and axial direction. At the right-hand side (D, E, F), a TIMS device with an octopolar RF field is shown which is again filled with a single ion species with different amounts of ions (D lowest amount, F highest amount). In the RF octopole field, the ion cloud of the single ion species has the shape of a cylindrical tube, i.e. the ion density is highest at an off-axis position. In the center part of the RF ion guide, the ions are pressed to the outside because of a space charge. With higher amounts of ions, the "ion cylinder" moves closer to the inner surface of the RF ion guide and is spread in axial direction. If more different ion species are present, the situation becomes somewhat chaotic, because the clouds are influencing each other, but during the scan of the TIMS device, the ion species leave the device one after another. Compared with the quadrupole field, the scanning unit using an octopolar RF field can take up about three to five times the number of ions before severe losses by the effect of space charge occur.

A TIMS device is preferably operated at a gas pressure of about two to three hectopascal; this gas pressure causes the kinetic energy of the ions to be damped. This procedure is called "thermalization". Ions with thermalized kinetic energies can be kept in higher multipole without severe losses.

The gas flow through the tube of a TIMS device is laminar and typically shows a parabolic velocity distribution downstream of the entrance region. Nitrogen may serve as a preferred gas. The vacuum conditions around the TIMS tube are chosen such that the maximum gas velocity amounts to about 100 to 150 meters per second, at a pressure of a few hectopascals. This velocity is only achieved near the axis, further off the velocity is considerably smaller, as indicated by the arrows (14) in FIG. 1.

TIMS was hitherto thought to require the ions to be trapped on the axis because they have to be driven over the electric DC field barrier by the central part of the gas flow at the apex of its parabolic velocity distribution. Otherwise, the relatively high ion mobility resolution was thought to decrease considerably. Surprisingly, it was found in experiments and simulations that this assumption was not correct.

FIG. 7 shows the spatial ion distribution of a single ion species at a high ion load in three different TIMS devices during accumulation (G, I, K) and scanning (H, J, L). At the left-hand side (G, H), a TIMS device with a pure quadrupolar RF field is shown. The ions are concentrated near the axis of the RF ion guide during the accumulation and scan phase. In the center (I, J), an octopolar RF field merges into a quadrupolar RF field such that ions are concentrated on the axis of the RF ion guide before they are released from the RF ion guide during the scan phase. In the pure octopolar RF field (right-hand side, K, L), the ions of cylindrical ion cloud are released without being concentrated on the axis of the RF ion guide. Despite the off-axis release, an acceptable mobility resolution can be achieved although mobility signals (peaks) are shifted somewhat along the ion mobility scale. Furthermore, the ion capacity of the RF ion guide with the pure octopolar RF field (K, L) at the space charge limit is typically three to six times higher than the ion capacity of the pure quadrupolar RF field at the space charge limit. Preferably, the ions are accumulated in an octopolar RF field and then focused onto the axis by a quadrupolar RF field at the end of the ramp of the electric DC field barrier as shown in the center (I, J). The transition from an octopolar to a quadrupolar RF field facilitates both a high ion capacity and a high mobility resolution with reduced, and even negligible, shifts of mobility peaks.

FIG. 8 shows ion trajectories in an RF ion guide of a preferred TIMS device during accumulation and scanning. The preferred TIMS device comprises an RF ion guide with a transition from an octopolar RF field to a quadrupolar RF field. The dots schematically represent the positions of ions that are first trapped and accumulated outside the axis in the octopole region and then concentrated on or near the axis downstream in the quadrupole region of the RF ion guide when they are released from the RF ion guide.

FIG. 9 shows a preferred PATIMS device according to the present invention. The electric DC profile shown in the upper part of the figure is equal to that of FIG. 2. The RF ion guide of the TIMS device generates an octopolar RF field (order N=4) at the entrance of the PATIMS device. The octopolar RF field transitions to a hexapolar RF field (N=3) in the scan unit and further to a quadrupolar RF field (N=2) at the plateau of the electric DC barrier of the scan unit. The RF quadrupole field (N=2) confines the ions near the axis of the RF ion guide adjacent to and at the apex of the electric DC field barrier. The RF ion guide may be fabricated from a flexible PCB foil rolled to a cylinder. It should be noted that the inserted hexapole field is by no means necessarily required; the octopole field may directly transition to a quadrupole field.

Usually, a transition from a higher order RF field to a lower order RF field is not symmetric. The acceptance profile of a multipole RF ion guide with lower number of poles does not commonly match the exit profile of a multipole RF ion guide with a higher number of poles. It is only by the friction with the flowing gas that ions enter the next multipole RF ion guide. FIG. 10 shows how a smooth transition from an octopolar RF field to a quadrupolar RF field can be generated, using an electrode system with 16 rows of inner electrodes. At the left-hand side, an octopolar RF field is generated by eight electrode rows (2, 4, 6, 8), whereby the rows (2) and (6) are supplied with a first phase of an RF voltage, and the rows (4) and (8) with a second phase of the RF voltage. The residual electrode rows (1, 3, 5, 7) are kept at ground potential. At the right-hand side, a quadrupolar RF field is generated by applying a first phase of an RF voltage to electrodes (2, 3, 4) and a second phase to electrodes (6, 7, 8). Electrodes (1) and (5) are kept at ground potential. A smooth transition from the octopolar RF field can be achieved by first feeding electrodes (3) and (7) with the quadrupolar RF voltage, generating a superposition of the octopolar RF field with a quadrupolar RF field, and then removing the octopolar RF voltages at electrodes (2, 4, 6, 8) and supplying the quadrupolar RF voltage to electrode groups (2, 3, 4) and (6, 7, 8).

There are other possible structures for smooth transitions between RF multipole fields of different orders. Publication US 2013/0306861 A1 (D. Papanastasiou and E. Raptakis; "Ion Guide with Different Order Multipolar Field Order Distributions Across Like Segments"), describes among others a transition from a dodecapole field (N=6) via a hexapolar field (N=3) to a quadrupolar field (N=2), using a structure with 24 rows of electrodes.

In addition to using higher order RF multipole fields, the ion capacity of a TIMS device may be increased by providing a larger diameter, at least in a part of the TIMS device. FIG. 11 shows a TIMS device with an RF ion guide (11b) which starts with a wide diameter and which generates a radial RF octopole field along an upstream portion. The RF ion guide (11b) then decreases in diameter and generates a radial RF quadrupole field in a downstream portion. Octopole and quadrupole fields are generated by a stack of apertured electrodes having the electrode structure presented in FIG. 10, allowing a smooth transition with partly overlapping RF fields of different orders. In the wider upstream portion, the gas flow (14a) is considerably slower than the gas flow (14b) in the narrower downstream portion. In the top of the figure, the equipotential lines of the radial RF fields are shown.

FIG. 12 shows a conical structure for a part of the TIMS device, rolled from a flexible PCB foil. The PCB foil can carry electric components for the distribution of the RF and DC voltages at the outside (not shown).

The invention claimed is:

1. A trapped ion mobility analyzer comprising an electric DC field barrier in the form of a ramp, a counteracting gas flow that drives ions against the electric DC field barrier, such that ions are trapped and separated along the ramp according to their mobilities, and an RF ion guide that generates an RF multipole field with an order higher than an RF quadrupolar field (N=2), such that ion density in the multipole field is highest away from an axis of the ion guide, allowing for accumulation of a relatively high number of ions without losses due to space charge effects.

2. The trapped mobility analyzer according to claim 1, wherein the RF multipole field with order N>2 extends along the electric DC field barrier.

3. The trapped ion mobility analyzer according to claim 2, wherein the RF ion guide additionally generates an RF quadrupolar field (N=2) which is substantially weaker than the RF multipole field with order N>2.

4. The trapped ion mobility analyzer according to claim 1, wherein the RF ion guide additionally generates an RF quadrupolar field (N=2) which is substantially weaker than the RF multipole field with order N>2 along a first portion of the ion guide and is substantially stronger than the RF multipole field with order N>2 along a second portion of the ion guide.

5. The trapped mobility analyzer according to claim 4, wherein the RF quadrupolar field is stronger than the RF multipole field with order N>2 adjacent to and/or on the apex of the electric DC field barrier.

6. The trapped mobility analyzer according to claim 5, wherein the RF quadrupolar field is stronger than the RF multipole field with order N>2 adjacent to the beginning and along at least a part of the a plateau of the electric DC field barrier.

7. The trapped mobility analyzer according to claim 1, wherein the RF multipole field with order N>2 transitions into an RF multipole field of lower order along the RF ion guide.

8. The trapped mobility analyzer according to claim 7, wherein the ion guide comprises a system of 16 rows of inner electrodes which are supplied with electric RF potentials and generates a transition from an octopolar RF multipole field into a quadrupolar RF field.

9. The trapped mobility analyzer according to claim 7, wherein the ion guide comprises a system of 24 rows of inner electrodes which are supplied with electric RF potentials and generates a transition from a dodecapolar RF field, optionally via a hexapolar RF field, into a quadrupolar RF field.

10. The trapped ion mobility analyzer according to claim 1, wherein the RF multipole field with order N>2 is one of a hexapolar (N=3), octopolar (N=4) and dodecapolar (N=6) RF field or an RF field of an ion guide with stacked apertured electrodes.

11. The trapped ion mobility spectrometer according to claim 1, wherein a flexible PCB board is rolled or folded to form the RF ion guide comprising the inner electrodes on one side and electric connections and components on the other side.

12. The trapped ion mobility analyzer according to claim 1, wherein a laminar gas flow is formed by a gas-tight tube which has a greater inner diameter at the entrance and a smaller inner diameter at the exit.

13. The trapped ion mobility spectrometer according to claim 12, wherein an RF multipole field of at least third order is generated in a segment of the tube with greater diameter, whereas a quadrupole RF field is prevailing in a segment with smaller diameter at the exit.

14. A mass spectrometric system comprising a trapped ion mobility analyzer comprising an electric DC field barrier in the form of a ramp, a counteracting gas flow that drives ions against the electric DC field barrier such that ions are trapped and separated along the ramp according to their mobilities, and an RF ion guide, the ion guide generating an RF multipole field with an order higher than a quadrupolar RF field (N=2), such that ion density in the multipole field is highest away from an axis of the ion guide, allowing for accumulation of a relatively high number of ions without losses due to space charge effects, and a downstream mass analyzer.

15. The mass spectrometric system according to claim 14, wherein the mass analyzer is one of a time-of-flight mass analyzer with orthogonal ion injection, an electrostatic ion trap, an RF ion trap, a quadrupole mass filter, and an ion cyclotron frequency mass analyzer.

16. The mass spectrometric system according to claim 14, wherein a quadrupole mass filter and a downstream fragmentation cell are positioned between the ion mobility analyzer and the mass analyzer.

17. A method for operating a trapped ion mobility analyzer, comprising the steps of:
 (a) generating ions in an ion source;
 (b) transferring the ions into an ion guide;
 (c) radially confining the ions in the ion guide by an RF multipole field with an order higher than an RF quadrupolar field (N=2), such that ion density in the multipole field is highest away from an axis of the ion guide, allowing for accumulation of a relatively high number of ions without losses due to space charge effects;

(d) axially trapping the ions in the ion guide by an electric DC field ramp and a counteracting gas flow that drives the ions against the electric DC field ramp such that the ions are separated along the ramp according to their mobilities; and (e) releasing the trapped ions from the ion guide according to their mobility by changing the electric DC field and/or the gas flow.

18. The method according to claim 17, wherein the amount of transferred ion species is so high that the ion density of at least one ion species is highest at an off-axis position along at least a part of the complete ion guide due to the space charge of the transferred ions.

19. The method according to claim 18, wherein the at least one ion species is released from the ion guide on an off-axis position.

20. The method according to claim 18, wherein the ions are radially confined by an RF multipole field with an order N>2 along an upstream part of the ion guide and by a quadrupolar RF field along a more downstream part of the ion guide, and wherein the ions are released from the ion guide on-axis at the more downstream part of the ion guide.

* * * * *